(12) United States Patent
Shukla et al.

(10) Patent No.: US 7,519,151 B1
(45) Date of Patent: Apr. 14, 2009

(54) ONLINE IGRT USING DIGITAL TOMOSYNTHESIS

(75) Inventors: Himanshu P. Shukla, Lafayette, CA (US); Jonathan Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/904,458

(22) Filed: Sep. 26, 2007

(51) Int. Cl.
*A61N 5/10* (2006.01)
(52) U.S. Cl. .......................................... 378/65; 378/62
(58) Field of Classification Search ............... 378/4–27, 378/65, 41, 62
See application file for complete search history.

(56) References Cited

U.S. PATENT DOCUMENTS

| | | | |
|---|---|---|---|
| 6,888,919 B2 | 5/2005 | Graf | 378/65 |
| 7,130,372 B2 | 10/2006 | Kusch et al. | 378/65 |
| 7,244,063 B2 | 7/2007 | Eberhard et al. | 378/196 |
| 7,245,698 B2 * | 7/2007 | Pang et al. | 378/65 |

OTHER PUBLICATIONS

G. Pang and J A Rowlands, "Just-in-time tomography (JiTT): a new concept for image-guided radiation therapy", Institute of Physics Publishing, Physics Medicine Biology, 50 (2005),, N323-N330, DOI: 10.1088/0031-9155/50/21/N05.
James T. Dobbins III and Devon J. Godfrey, Topical Review, "Digital x-ray tomosynthesis: current state of the art and clinical potential", Institute of Physics Publishing, Phys Medicine Biology, 48 (2003), R65-R106, PII: S0031-9155(03)32561-8.
Shusuke Sone, MD et al., "Development of a High-Resolution Digital Tomosynthesis System and Its Clinical Application", Radiographics, 1991, vol. 11, No. 5, pp. 807-822.

* cited by examiner

*Primary Examiner*—Courtney Thomas

(57) ABSTRACT

A system includes movement of a treatment delivering x-ray source to a treatment position, creation of projection images of a target using an imaging x-ray source while the treatment delivering x-ray source is disposed at the treatment position, and performance of digital tomosynthesis on the projection images while the treatment delivering x-ray source is disposed at the treatment position to generate a cross-sectional image of the target. A characteristic of an x-ray beam to be delivered by the treatment delivering x-ray source may be automatically modified based on the cross-sectional image. In some aspects, the imaging x-ray source translates in a plane normal to a beam axis of the treatment delivering x-ray source at the treatment position, and pivots about an axis passing through the imaging x-ray source during creation of projection images. Creation of the projection images may alternatively include emission of a respective x-ray beam from each of a plurality of sources of the imaging x-ray source, wherein the imaging x-ray source is stationary with respect to the treatment delivering x-ray source during creation of the projection images.

25 Claims, 10 Drawing Sheets

ONLINE IGRT USING DIGITAL TOMOSYNTHESIS

BACKGROUND

1. Field

The embodiments described below relate generally to the delivery of therapeutic radiation to a patient. More specifically, some embodiments are directed to treatment verification systems used in conjunction with such delivery.

2. Description

Conventional radiation treatment directs a radiation beam toward a tumor located within a patient. The radiation beam delivers a dose of therapeutic radiation to the tumor according to a pre-established treatment plan. The delivered radiation kills cells of the tumor by causing ionizations within the cells.

Radiation treatment plans are designed to maximize radiation delivered to a target while minimizing radiation delivered to healthy tissue. These goals might not be achieved if the radiation is not delivered exactly as required by the treatment plan. More specifically, errors in radiation delivery can result in low irradiation of tumors and high irradiation of sensitive healthy tissue.

Delivery errors may arise from many sources. For example, a patient position may vary from that designated by a treatment plan, and/or internal patient anatomy may be displaced with respect to external visible markers. Quality assurance procedures are typically performed in order to detect and correct potential radiation delivery errors. These procedures are particularly time-consuming and often inefficient, and are therefore only performed periodically prior to delivery of a treatment fraction.

Current trends point to hypofractionated delivery in which high doses are delivered per each treatment fraction. These trends increase the necessity of precise positioning during any given treatment. Delivery errors may also be identified after treatment, in which case a next fraction may be modified in an attempt to account for the errors. The latter approach is particularly troublesome, as unintentional delivery of radiation to sensitive tissues obviously cannot be undone.

In view of the foregoing, what is needed is a system to efficiently identify potential delivery errors so that treatment may be modified and/or suspended. It is further desirable to identify such errors prior to delivery of each beam of a treatment fraction.

SUMMARY

To address at least the foregoing, some embodiments provide a system, method, apparatus, and means to move a treatment delivering x-ray source to a treatment position, create projection images of a target using an imaging x-ray source while the treatment delivering x-ray source is disposed at the treatment position, and perform digital tomosynthesis on the projection images while the treatment delivering x-ray source is disposed at the treatment position to generate a cross-sectional image of the target. According to some aspects, a characteristic of an x-ray beam to be delivered by the treatment delivering x-ray source is modified based on the cross-sectional image.

In some aspects, creation of the projection images includes movement of the imaging x-ray source independently of the treatment delivering x-ray source. Movement of the imaging x-ray source may include translation of the imaging x-ray source in a plane normal to a beam axis of the treatment delivering x-ray source at the treatment position, and pivoting of the imaging x-ray source about an axis passing through the imaging x-ray source. Creation of the projection images, in some aspects, may further include movement of an x-ray detector in a plane normal to the beam axis of the treatment delivering x-ray source.

Creation of the projection images may alternatively include emission of a respective x-ray beam from each of a plurality of sources of the imaging x-ray source, wherein the imaging x-ray source is stationary with respect to the treatment delivering x-ray source during creation of the projection images.

Some aspects may include movement of the treatment delivering x-ray source to a second treatment position, creation of second projection images using the imaging x-ray source while the treatment delivering x-ray source is disposed at the second treatment position, and performance of digital tomosynthesis on the second projection images while the treatment delivering x-ray source is disposed at the second treatment position to generate a second cross-sectional image of the target.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by the inventors for carrying out the described embodiments. Various modifications, however, will remain readily apparent to those in the art.

Figure 1:
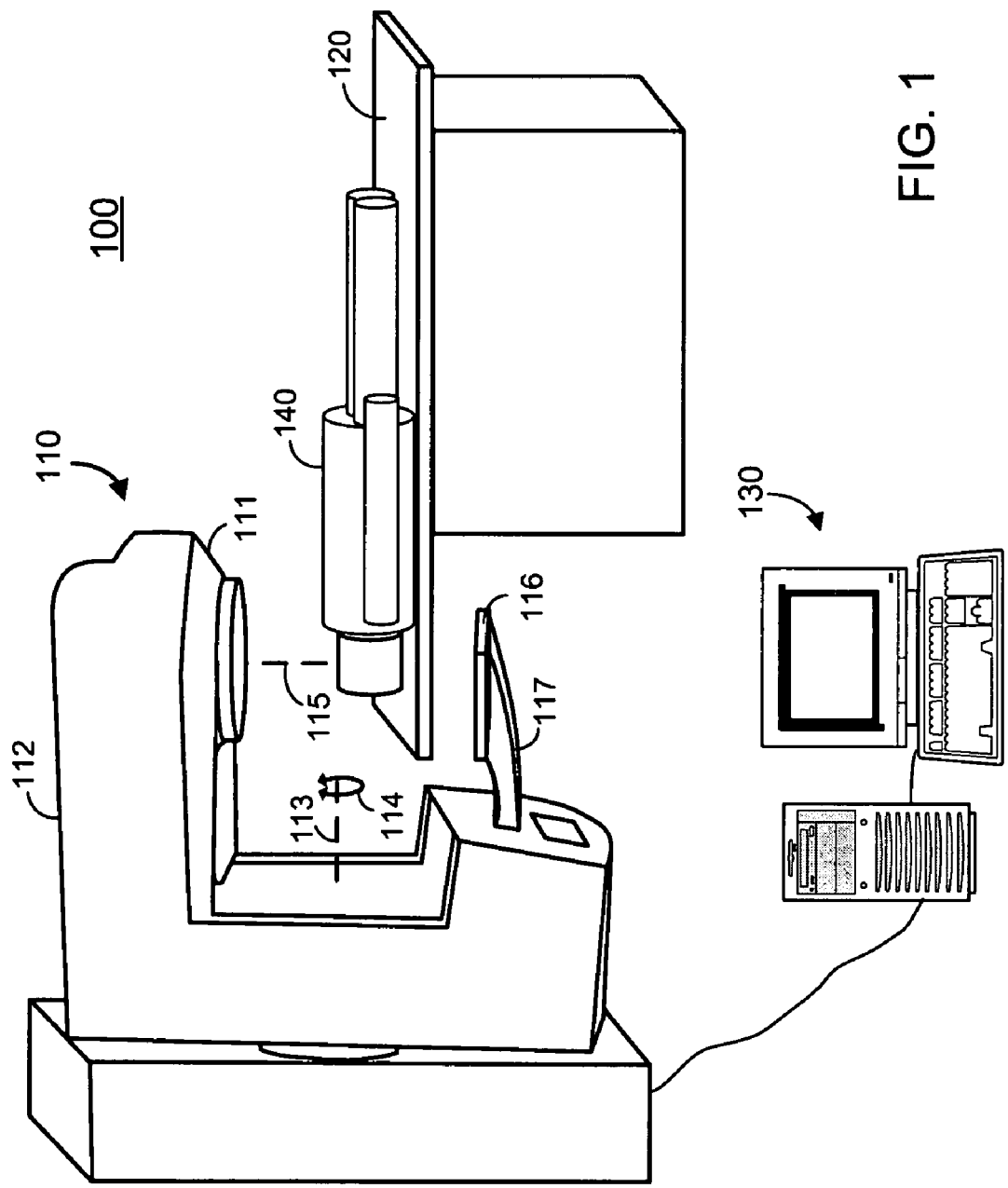
FIG. 1 is a perspective view of a radiation treatment room according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver a treatment beam of x-rays to a target volume of beam object 140. In this regard, beam object 140 may comprise a patient positioned to receive the treatment beam according to a radiation treatment plan. The elements of treatment room 100 may be employed in other applications according to some embodiments.

Linac 110 may comprise an in-line kilovoltage/megavoltage radiotherapy delivery system such as the ARTISTE™ system from Siemens Medical Systems, but embodiments are not limited thereto. Linac 110 generates and emits a treatment x-ray beam from treatment head 111. Treatment head 111 is therefore considered a treatment delivering x-ray beam source and includes a beam-emitting device for emitting a beam during calibration, verification, and/or treatment. The radiation beam may comprise electron, photon or any other type of radiation. According to some embodiments, the beam exhibits energies in the megavoltage range (i.e. >1 MeV) and may therefore be referred to as megavoltage beam.

Also included within treatment head 111 is a beam-shielding device, or collimator, for shaping the beam and for shielding sensitive surfaces from the beam. The collimator may be rotated and various elements of the collimator may be positioned according to a treatment plan. The collimator may thereby control a cross-sectional shape of the beam.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment, treatment head 111 emits a divergent beam of megavoltage x-rays. The beam is emitted towards an isocenter of linac 110. The isocenter is located at the intersection of beam axis 115 and gantry axis 113. Due to divergence of the beam and the shaping of the beam by the aforementioned beam-shaping devices, the beam may deliver radiation to a volume of beam object 140 rather than only through the isocenter.

Table 120 supports beam object 140 during radiation treatment. Table 120 may be adjustable to assist in positioning a treatment area of beam object 140 at the isocenter of linac 110. Table 120 may also be used to support devices used for such positioning, for calibration and/or for verification.

Imaging device 116 may acquire projection images before, during and/or after radiation treatment. For example, imaging device 116 may be used to acquire images for verification and recordation of a target volume position and of an internal patient portal to which radiation is delivered.

Imaging device 116 may be attached to gantry 112 in any manner, including via extendible and retractable housing 117. Rotation of gantry 112 may cause treatment head 111 and imaging device 116 to rotate around the isocenter such that isocenter remains located between treatment head 111 and imaging device 116 during the rotation. Imaging device 116 may comprise any system to acquire an image based on received x-rays.

Figure 2:
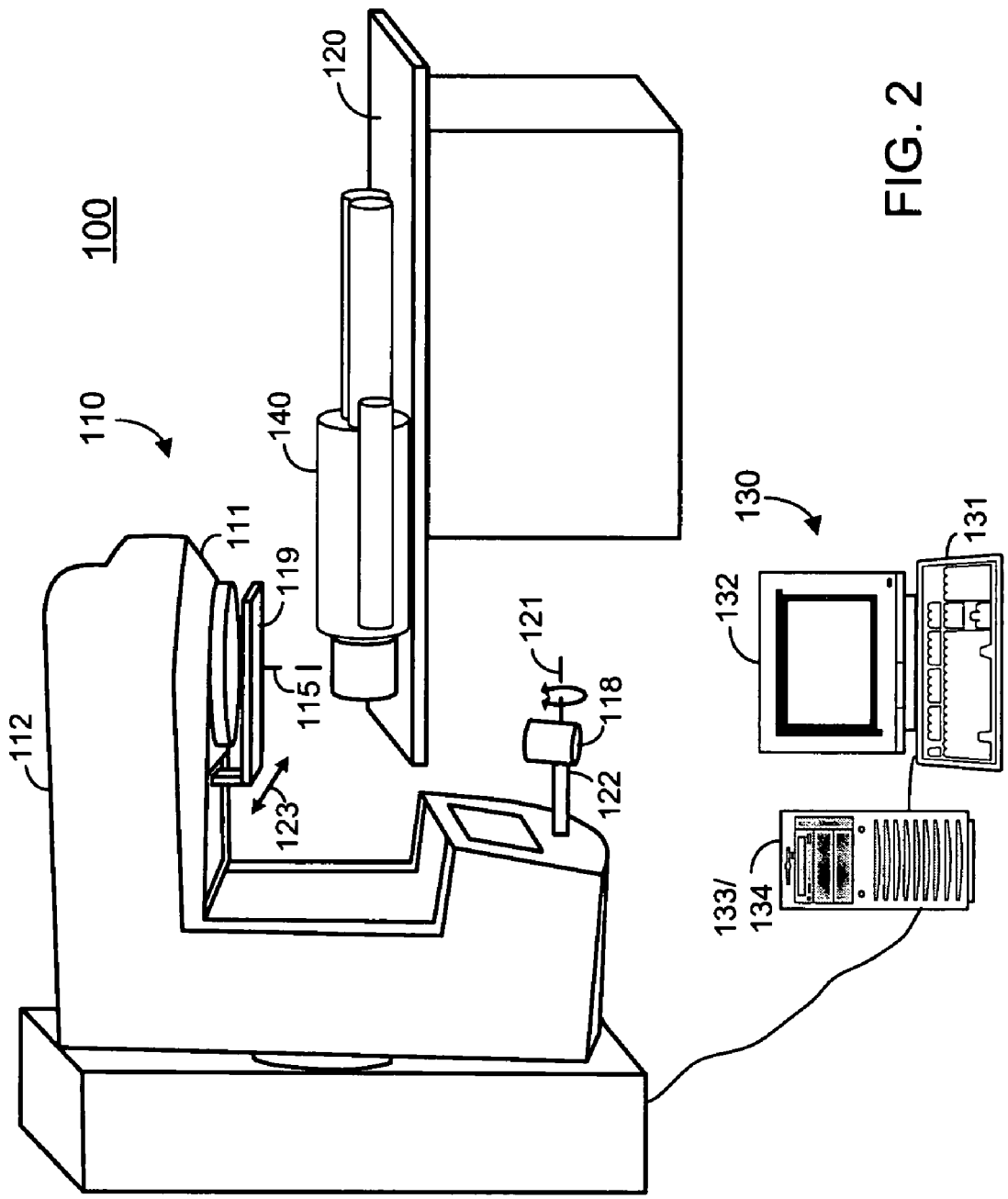
FIG. 2 is a perspective view of a radiation treatment room according to some embodiments.

FIG. 2 illustrates the elements of treatment room 100 in a second configuration. Imaging device 116 has been retracted into a lower portion of gantry 112 and imaging x-ray source 118 has been extended therefrom. Also shown is x-ray detector 119 which has been deployed from a cavity of gantry 112 to a position in front of treatment head 111.

According to some embodiments, treatment delivering x-ray source 111 moves to a treatment position, and projection images of a target within object 140 are acquired using imaging x-ray source 118 and x-ray detector 119 while treatment delivering x-ray source 111 is disposed at the treatment position. Processor 133 of computer system 130 then performs digital tomosynthesis on the projection images to generate a cross-sectional image of the target. The foregoing features may provide efficient verification of a target position immediately prior to treatment via a treatment perspective as defined by the current gantry location. Detailed examples of some embodiments are provided below.

Imaging x-ray source 118 is coupled to gantry 112 via extension 122. In some embodiments, extension 122 may allow source 118 to rotate about axis 121 extending through source 118 and to translate in a plane perpendicular to beam axis 115. Source 118 may be coupled to extension 122 by a pivoting joint to allow such rotation. Imaging x-ray source 118 may comprise any suitable single or multi-source device to emit imaging radiation, including but not limited to a conventional x-ray tube. In some embodiments, x-ray source 118 emits kilovoltage radiation having energies ranging from 50 to 150 keV.

X-ray detector 119 is adapted to translate in a plane perpendicular to beam axis 115 as shown by arrow 123. In some embodiments, x-ray detector 119 is a flat-panel imaging device using a scintillator layer and solid-state amorphous silicon photodiodes deployed in a two-dimensional array. According to some embodiments, a single x-ray detector is used to acquire projection images based on x-rays emitted from a treatment delivering x-ray source (e.g., treatment head 111) and to acquire projection images based on x-rays emitted from a separate imaging x-ray source (e.g., imaging source 118).

In operation, the scintillator layer receives photons and generates light in proportion to the intensity of the received photons. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

X-ray detector 119 may comprise other types of imaging devices. For example, X-ray radiation may also be converted to and stored as electrical charge without use of a scintillator layer. In such imaging devices, x-rays are absorbed directly by an array of amorphous selenium photoconductors. The photoconductors convert the x-rays directly to stored electrical charge that comprises an acquired image of a radiation field.

The charge developed and stored by x-ray detector 119 represents radiation intensities at each location of a radiation field produced by a beam emitted from imaging x-ray source 118. Since object 140 is located between source 118 and x-ray detector 119, the radiation intensity at a particular location represents the attenuative properties of tissues along a divergent line between source 118 and the particular location. The set of radiation intensities acquired by x-ray detector 119 may therefore comprise a two-dimensional projection image of these tissues.

Such a projection image, taken alone, is of limited use in determining a position of a particular internal target. Specifically, the target will likely be obscured by structures located between the target and x-ray source 118 and by structures located between the target and x-ray detector 119. Some conventional systems attempt to determine a position of a target by generating a three-dimensional cone beam computed tomography (CBCT) image prior to treatment. Generation of a CBCT image requires acquisition of many projection images from many perspectives along a ≧180 degree arc surrounding the target. Such acquisition is particularly time-consuming and requires a significant amount of mechanical motion, particularly when delivering a multi-beam treatment fraction. A will be described below, digital tomosynthesis techniques may be used to produce a cross-sectional image of a particular plane viewed from a particular perspective (e.g., a treatment perspective) based on a far more limited set of projection images.

Operator console 130 includes input device 131 for receiving instructions from an operator and output device 132, which may be a monitor for presenting operational parameters of linac 110, images acquired by imaging device 116, images acquired by x-ray detector 119, CT images used for treatment planning, interfaces for receiving operator instructions, and/or operator alerts. According to some embodiments, output device 132 may present an alert notifying an operator of an error during treatment delivery.

Input device 131 and output device 132 are coupled to processor 133 and storage 134. Processor 133 may execute program code to perform any of the determinations and generations described herein, and/or to cause linac 110 to perform any of the process steps described herein.

Storage 134 may also store program code to generate and/or modify a treatment plan according to some embodiments. Accordingly, storage 134 may also store radiation treatment plans in accordance with any currently- or hereafter-known format. The treatment plans may comprise scripts that are automatically executable by elements of room 100 to provide treatment fractions. Each beam of each fraction of each treatment plan may require treatment head 111 to be positioned in a particular manner with respect to a patient, a collimator to be configured to define a particular beam shape, and a megavoltage x-ray source to deliver a beam having a particular energy profile.

Operator console 130 may be in a room other than treatment room 100, in order to protect its operator from radiation. For example, treatment room 100 may be heavily shielded, such as a concrete vault, to shield the operator from radiation generated by linac 110.

A hardware environment according to some embodiments may include less or more elements than those shown in FIGS. 1 and 2. In addition, embodiments are not limited to the devices and/or to the illustrated environment.

Figure 3:
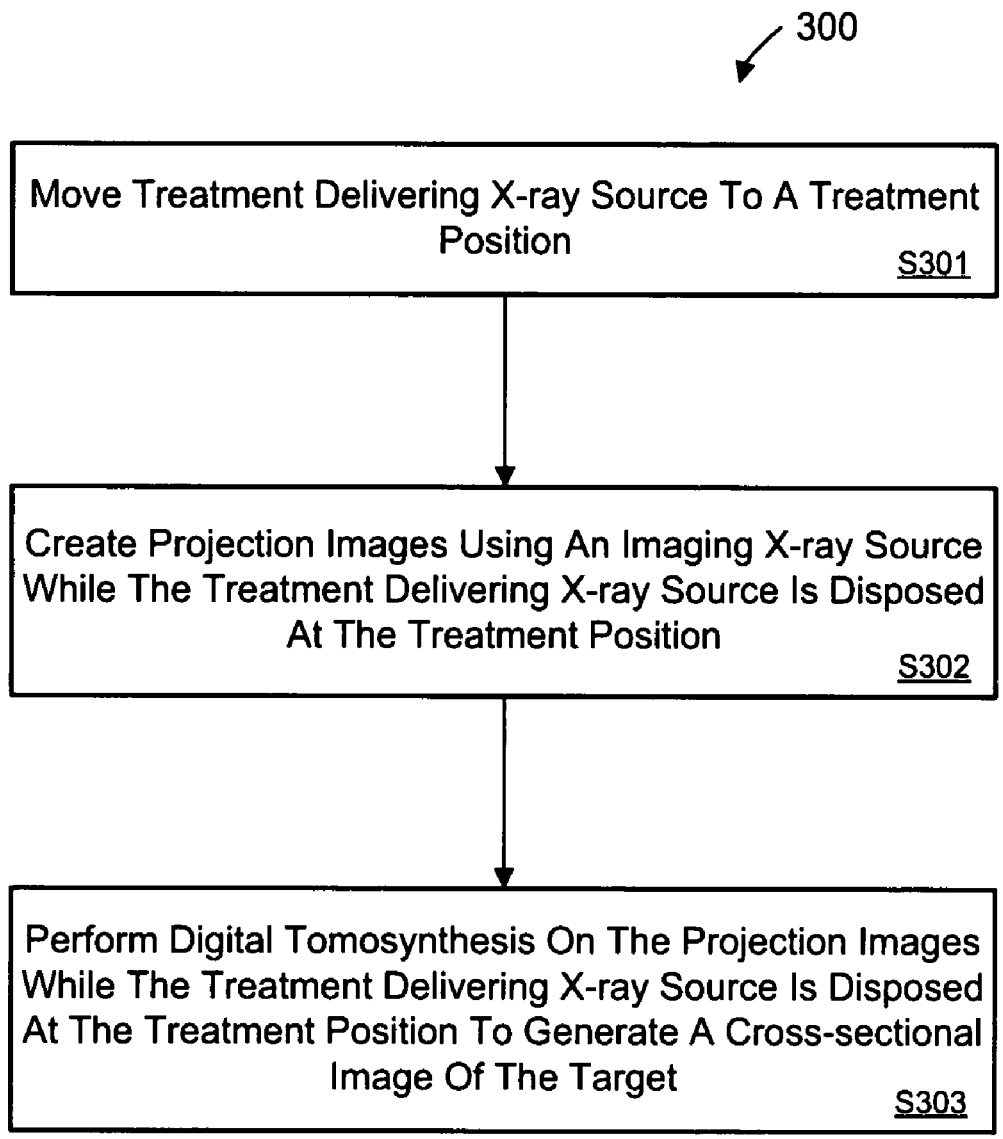
FIG. 3 comprises a flow diagram illustrating process steps according to some embodiments.

FIG. 3 is a flow diagram of a process according to some embodiments. Process 300 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 300 may be performed after a patient has been placed on a treatment table and is awaiting treatment. At S301, a treatment delivering x-ray source is moved to a treatment position.

Figure 4A:
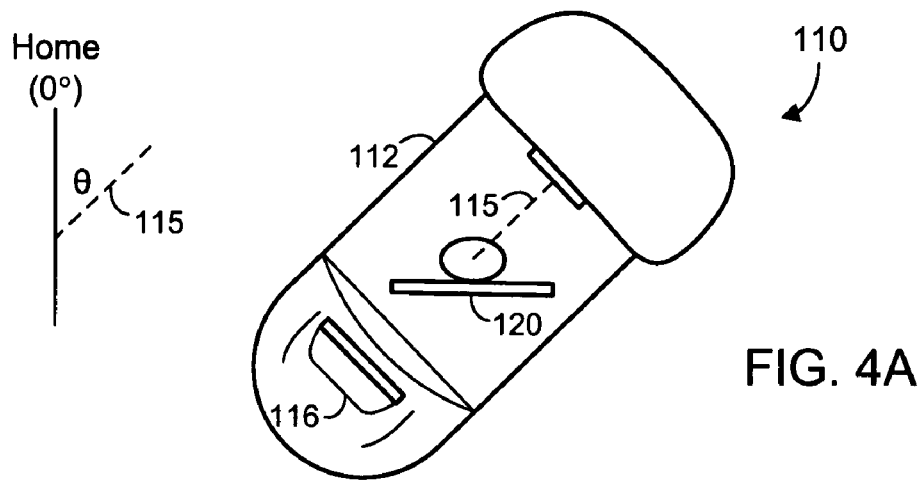
FIGS. 4A through 4C comprise front views of a treatment device to illustrate process steps according to some embodiments.
Figure 4B:
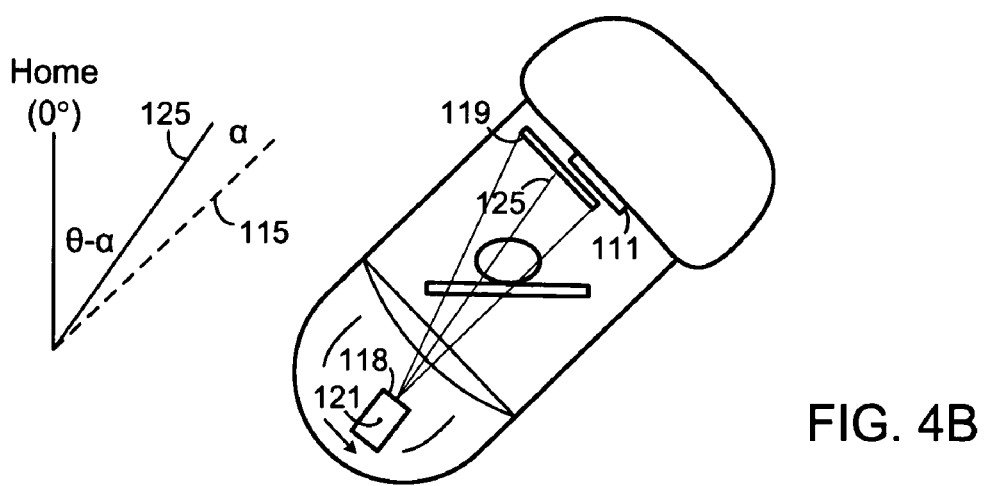

FIGS. 4A through 4B illustrate S301 according to some embodiments. In FIG. 4A, gantry 112 of linac 110 has been rotated such that beam axis 115 is disposed at delivery angle $\theta$ with respect to a "home" position (0°). Angle $\theta$ represents a position from which a next treatment beam is to be delivered according to a treatment plan. Imaging device 116, x-ray detector 119 and kilovoltage x-ray source 118 are deployed as shown in FIG. 1, but embodiments are not limited thereto.

At S302, projection images are created using an imaging x-ray source while the treatment delivering x-ray source is disposed at the treatment position. Any suitable number of projection images may be created at S302 from any number of projection angles.

FIG. 4B illustrates the creation of a projection image according to some embodiments. X-ray detector 119 and imaging x-ray source 118 are deployed as shown in FIG. 2 and treatment head 111 remains disposed at the treatment position. However, imaging x-ray source 118 has rotated about axis 121 and has translated in a plane normal to axis 115 as illustrated by the arrow. Detector 119 has also translated in a plane normal to axis 115. Imaging x-ray beam axis 125 extends from a center of source 118 to a center of detector 119 and defines an angle $\alpha$ with beam axis 115 as shown in the ray diagram of FIG. 4B. Imaging x-ray beam axis 125 is therefore disposed at angle $\theta$-$\alpha$ with respect the home position.

Figure 4C:
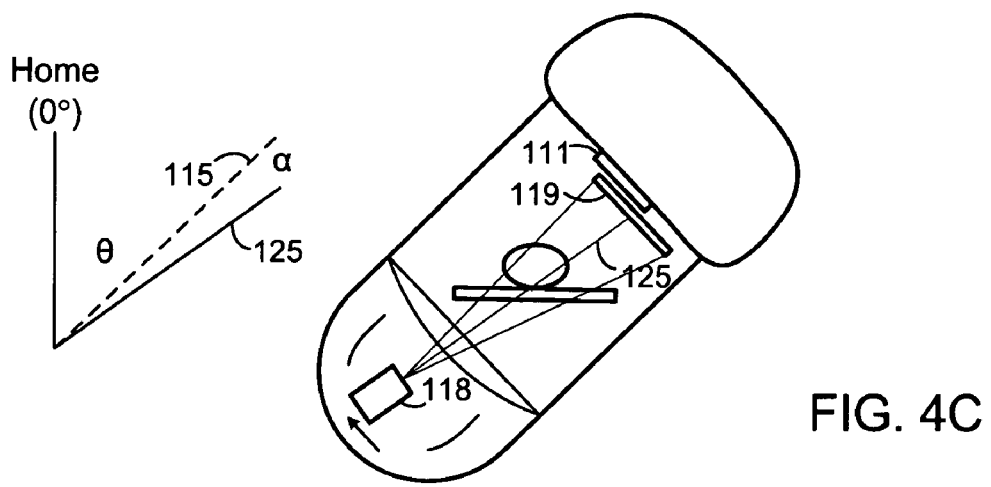

Creation of a second projection image is illustrated in FIG. 4C. Kilovoltage x-ray source 118 has rotated and translated to the illustrated position, and detector 119 has translated to its illustrated position. Treatment head 111 remains disposed at the treatment position. Imaging x-ray beam axis 125 again extends from a center of source 118 to a center of detector 119 and defines an angle $\alpha$ with beam axis 115. However, beam axis 125 is now disposed at angle $\theta$+$\alpha$ with respect to the home position.

Some embodiments may include creation of a projection image at each of several angular intervals between the angles illustrated in FIGS. 4B and 4C (i.e., $\theta$-$\alpha$ and $\theta$+$\alpha$). A projection image, for example, may be created at each degree between $\theta$-$\alpha$ and $\theta$+$\alpha$. A greater number of unique projections spread out over a fixed amount of coverage may result in a higher-quality cross-sectional image than a lesser number. Creation of the projection images need not be symmetric around $\theta$ in some embodiments. That is, projection images may be created at each of several intervals between $\theta$-$\beta$ and $\theta$+$\gamma$. According to some embodiments, $10°<\alpha,\beta,\gamma<45°$.

The projection images are created by emitting a suitable imaging x-ray beam from source 118 and operating detector 119 to acquire a two-dimensional set of radiation intensities. The intensities represent the attenuative properties of tissues between source 118 and detector 119.

The projection images created at S302 may be corrected or transformed based on characteristics of detector 119 and/or based on the illustrated geometries. In the latter regard, the projection images may be modified to account for the different distances over which different portions of the emitted beams travel to reach detector 119.

Next, at S303, digital tomosynthesis is performed on the projection images to generate a cross-sectional image of the target while the treatment delivering x-ray source is disposed at the treatment position. Various digital tomosynthesis reconstruction algorithms have been developed, which include filtered back projection algorithms. For example, the projection images may be filtered with a Ram-Lak filter before back projection. The resulting cross-sectional image may be orthogonal to a treatment x-ray beam axis at a linac isocenter.

Digital tomosynthesis may consume significantly less time than CBCT, while providing a reconstructed partial cross-sectional image that is orthogonal to the principal beam axis of a megavoltage x-ray source at a particular gantry angle $\theta$. The reconstructed image may also include the isocenter, if the geometry of projection image acquisition is isocentric. The image could therefore be used to immediately determine whether to deliver and/or modify planned treatment based on various criteria. In comparison to two-dimensional projection images alone, digital tomosynthesis provides improved delineation of depth-resolved tissue boundaries due to the reduced influence of under- and overlying structures.

Figure 5:
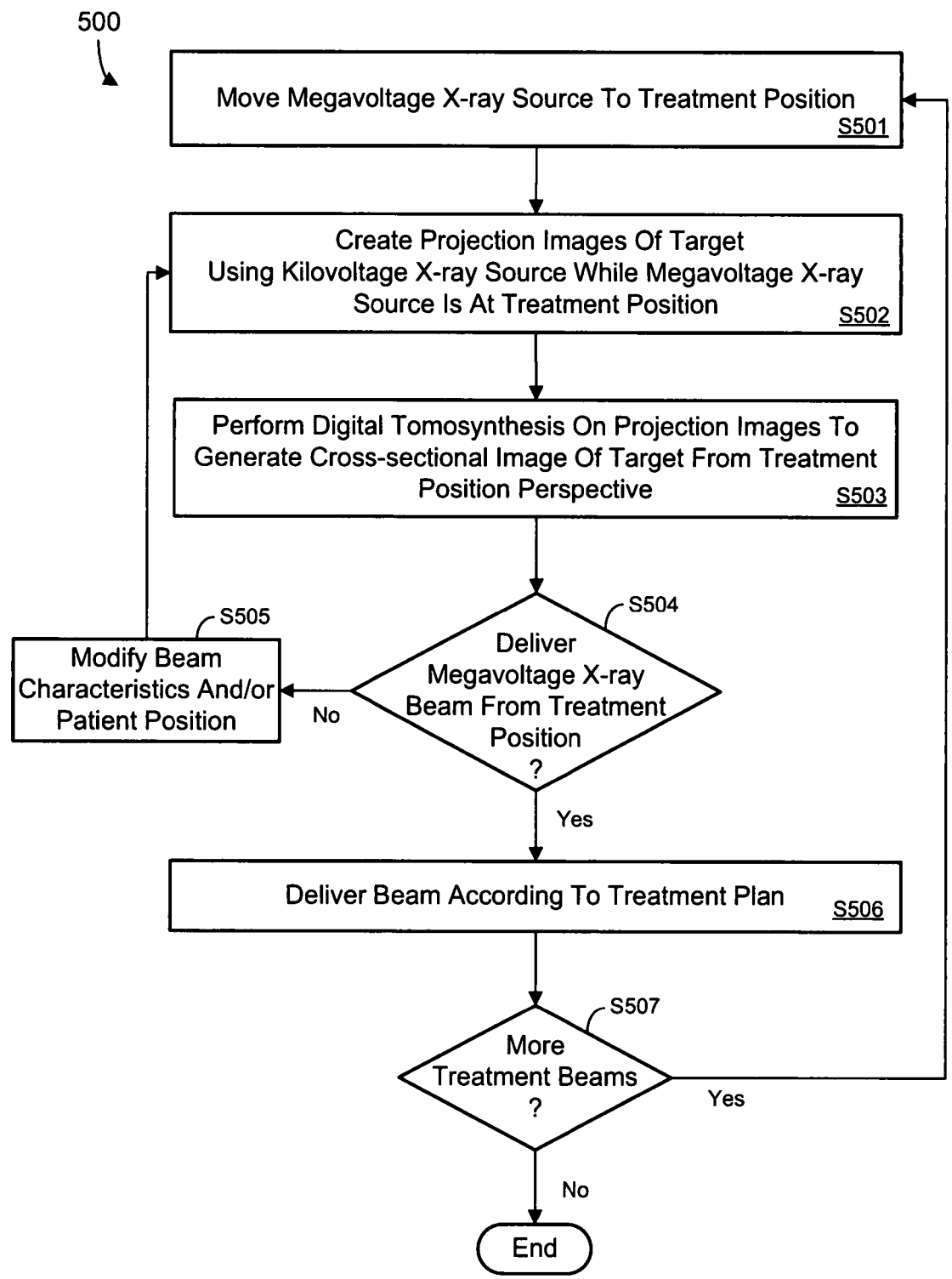
FIG. 5 comprises a flow diagram illustrating process steps according to some embodiments.

Process 500 of FIG. 5 may also be executed by any suitable combination of hardware and software. Some embodiments of process 500 include process 300 of FIG. 3, but embodiments are not limited thereto.

Process 500 may be preceded any suitable quality assurance procedures. In some embodiments, process 500 is preceded by acquisition of correction images for performing corrections on images acquired by kilovoltage x-ray detector 119. These corrections may comprise offset correction to account for dark current effects, gain correction to account for variations in pixel sensitivity, and dead pixel correction to account for malfunctioning pixels.

A treatment plan is also established prior to process 500. The treatment plan may define multiple treatment fractions, each of which includes one or more discrete beams to be delivered. For each beam, the treatment plan may specify a gantry rotation angle, a collimator configuration, a beam profile, and a cross-sectional image of a target at a gantry isocenter and orthogonal to the beam axis. The cross-sectional image may be generated based on a CT image used to create the treatment plan. Embodiments are not limited to the foregoing type of treatment plan, although may be particularly suitable in cases where the gantry remains static during beam delivery. For example, each beam can be static or moving, and/or may exhibit multiple radiation shapes delivered discretely (i.e., segments or ports) or continuously. According to some treatment plans, one or more plan parameters may change continuously and simultaneously (e.g., gantry position, collimator size/shape/rotation, patient support, imaging).

Initially, at S501, a megavoltage x-ray source is moved to a treatment position. As described above, such movement may be controlled by processor 133 by executing a treatment plan script. For purposes of the present example, it will be assumed that the megavoltage x-ray source is moved to gantry position θ of FIG. 4A.

Projection images of a target are created at S502 using a kilovoltage x-ray source while the megavoltage x-ray source remains at the treatment position. Continuing the present example, kilovoltage x-ray source 118 may translate and rotate about axis 121, and detector 119 may translate at S502 to create a projection image at each angular degree between and including θ-α of FIG. 4B and θ+α of FIG. 4C.

Digital tomosynthesis is performed on the projection images at S503 to generate a cross-sectional image of the target from the perspective of the treatment position. The cross-sectional image is orthogonal to the megavoltage x-ray source beam axis at the target. The cross-sectional image may include the isocenter of the megavoltage x-ray source in some embodiments. Prior to S503, the projection images may be corrected or transformed based on the aforementioned correction images and/or based on the geometries shown in FIGS. 4B and 4C. The digital tomosynthesis algorithm used to generate the cross-sectional image may additionally or alternatively account for these geometries in some embodiments.

At S504, it is determined whether to deliver a megavoltage x-ray beam from the treatment position based on the cross-sectional image. According to some embodiments of S504, output device 132 displays the cross-sectional image and a reference image (e.g., an expected cross-sectional image via the treatment plan) to an operator and processor 133 waits for an operator instruction to deliver the beam. In some embodiments, processor 133 submits the cross-sectional image to an automatic validation algorithm to check for consistency between the reference image and the cross-sectional image.

The reference image may be generated during creation of the treatment plan. For example, a three-dimensional CT image is loaded into a treatment planning system and a treatment plan is created based on the image. A delivery vector (i.e., treatment gantry angle) is determined for one or more treatment beams of each treatment fraction of the treatment plan. For each delivery vector, a set of projection images is generated using a divergent virtual source-detector model (e.g., such as that used for a Digitally Reconstructed Radiograph (DRR)). The set of projection images simulates the digital tomosynthesis projection images described above with respect to S502. The reference image for a particular delivery vector is then generated by applying digital tomosynthesis to the set of projection images associated with the particular delivery vector.

Flow proceeds to S505 if it is determined at S504 not to deliver the megavoltage x-ray beam. Characteristics such as the shape of the beam to be delivered and/or the patient position may be modified at S505. Such modification may be based on the cross-sectional image generated at S503. More particularly, the modifications may be based on differences between the generated cross-sectional image and the reference image.

Flow continues to S506 if the determination at S504 is affirmative. A megavoltage x-ray beam is delivered according to the treatment plan at S506. According to some embodiments of S506, gantry 112 may be rotated to angle θ if not already there, a collimator may be configured according to the treatment plan, linac 110 is controlled to generate a megavoltage x-ray beam having an energy and characteristics specified by the treatment plan.

At S507, it is determined whether the present treatment fraction includes additional treatment beams. If not, process 500 terminates. If more treatment beams are specified, flow returns to S501 to move the megavoltage x-ray source to a new treatment position. The new treatment position may be identical to the previous treatment position in some embodiments.

Figure 6A:
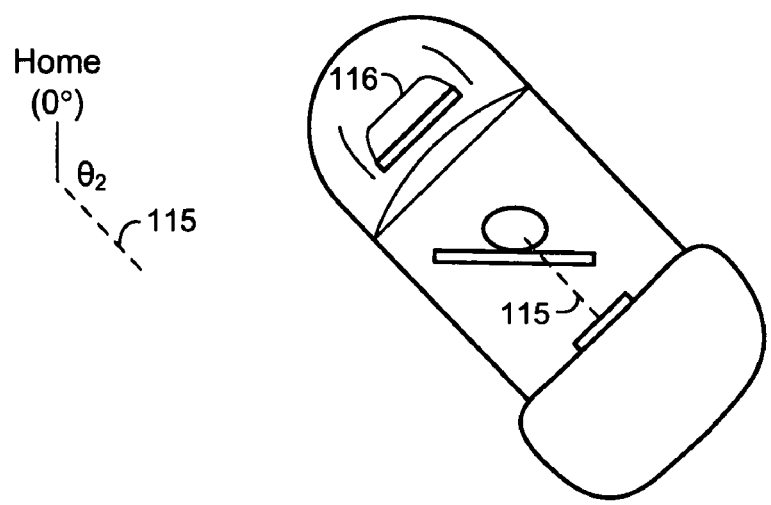
FIGS. 6A through 6C comprise front views of a treatment device to illustrate process steps according to some embodiments.
Figure 6B:
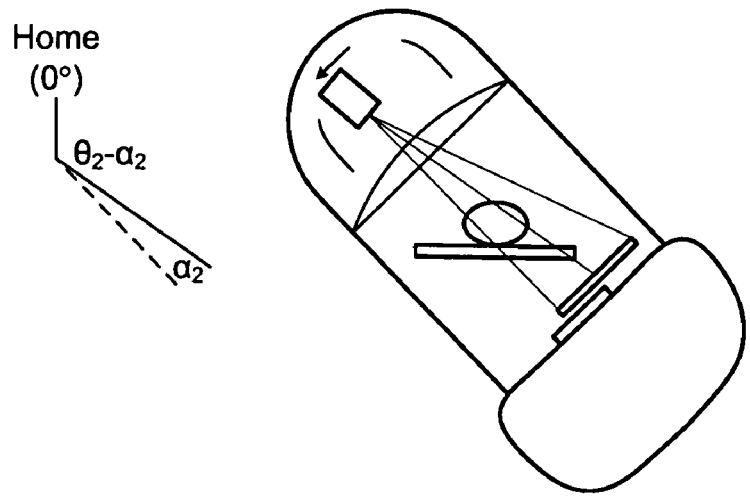
Figure 6C:
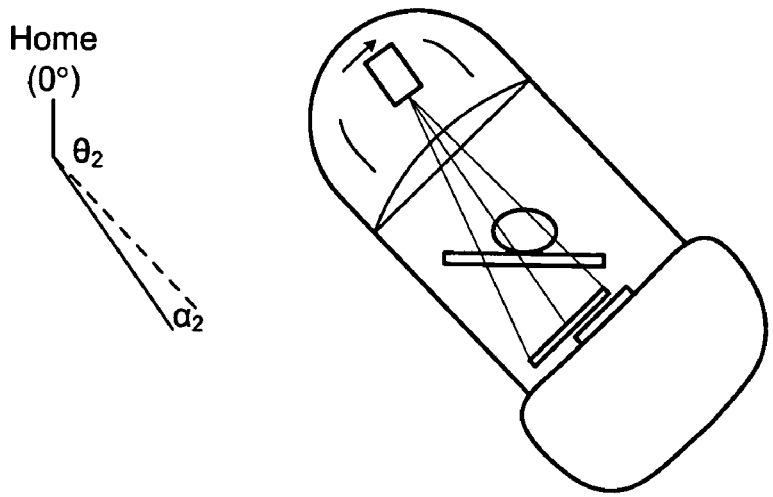

Flow continues from S501 as described above. FIGS. 6A through 6C illustrate a continuation of the previous example of process 500. FIG. 6A shows a new treatment position in which beam axis 115 is at new angle $\theta_2$ with respect to the home position. Imaging device 116 is deployed and source 118/detector 119 are not deployed because a megavoltage x-ray beam was recently delivered at S506.

FIGS. 6B and 6C illustrate subsequent creation of projection images at S502. As shown, the projection images are created by translating and rotating kilovoltage x-ray source 118, and by translating detector 119. Creation of the projection images may proceed over the arc from angle $\theta_2-\alpha_2$ to $\theta_2+\alpha_2$. The arc over which projection images are created may be traversed in the counter-clockwise direction in some embodiments.

According to some embodiments, projection images of a target may be created by moving a kilovoltage x-ray source independently of a megavoltage x-ray source. The independent movement of the kilovoltage x-ray source may comprise any type of movement(s) relative to the megavoltage x-ray source (which itself may be moving), and may be accomplished by any system that is or becomes known.

Figure 7:
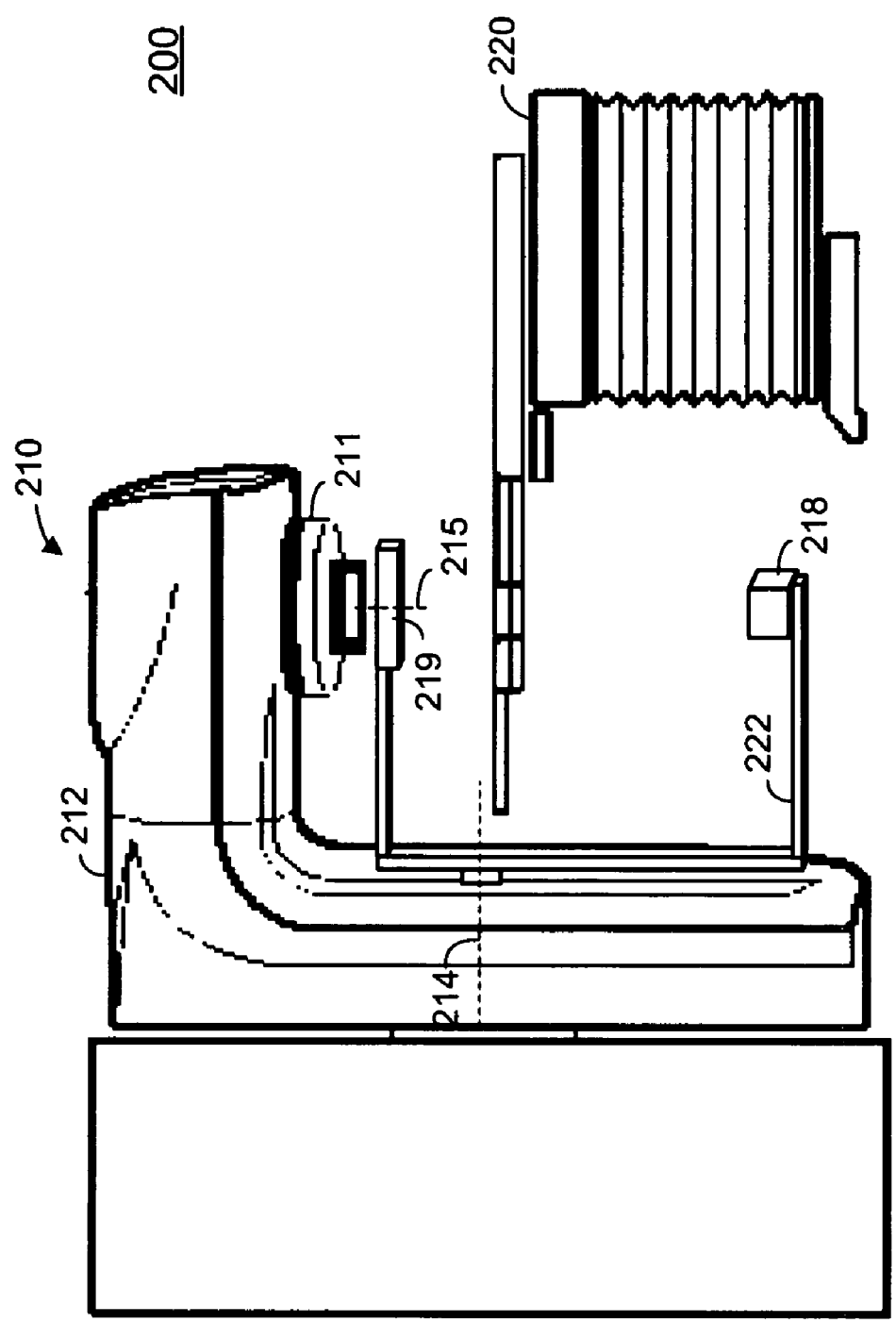
FIG. 7 is a perspective view of a radiation treatment room according to some embodiments.

FIG. 7 illustrates treatment room 200 according to some embodiments. Treatment room 200 includes linac 210 and table 220. Linac 210 includes treatment head 211 to deliver a treatment x-ray beam having beam axis 215, and gantry 212 to rotate about axis 214. Also included are imaging x-ray source 218 and x-ray detector 219. Each of the above-mentioned elements of room 200 may be embodied by any of the alternatives described above with respect to similarly-named elements of treatment room 100.

Imaging x-ray source 218 and x-ray detector 219 may be moveable independently of treatment head 211. According to one specific example of the foregoing, support 222 is rotatable to rotate imaging x-ray source 218 and x-ray detector 219 around axis 214 independent from any rotation of gantry 212. In some embodiments, support 222 is rotatable to rotate imaging x-ray source 218 and x-ray detector 219 around an axis different from axis 214.

Support 222 may comprise any suitable structure. Support 222 may comprise a single integral element or several elements. Support 222 may include various elements for coupling to imaging x-ray source 218 and/or to imaging x-ray detector 219. Support 222 may be coupled to gantry 212 by a rotating coupling such as, but not limited to, a rotational bearing to facilitate the rotation of support 222 independently of any rotation of gantry 212. According to some embodiments, support 222 comprises a currently- or hereafter-known "U-arm" for supporting and x-ray tube and an x-ray detector.

Figure 8A:
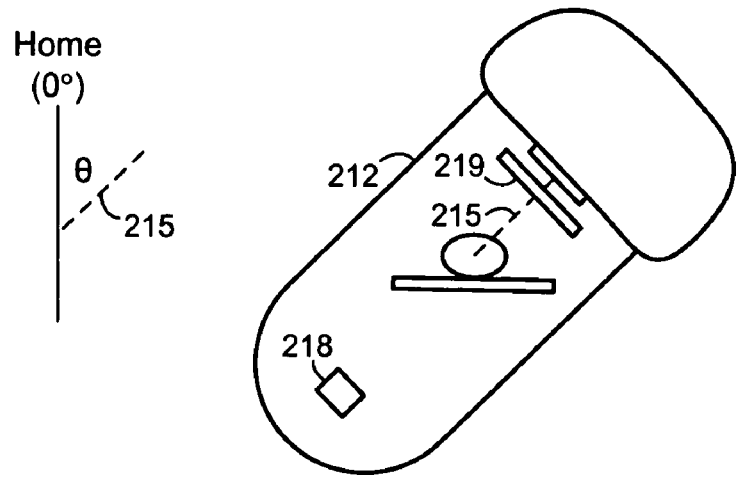
FIGS. 8A through 8C comprise front views of a treatment device to illustrate process steps according to some embodiments.
Figure 8B:
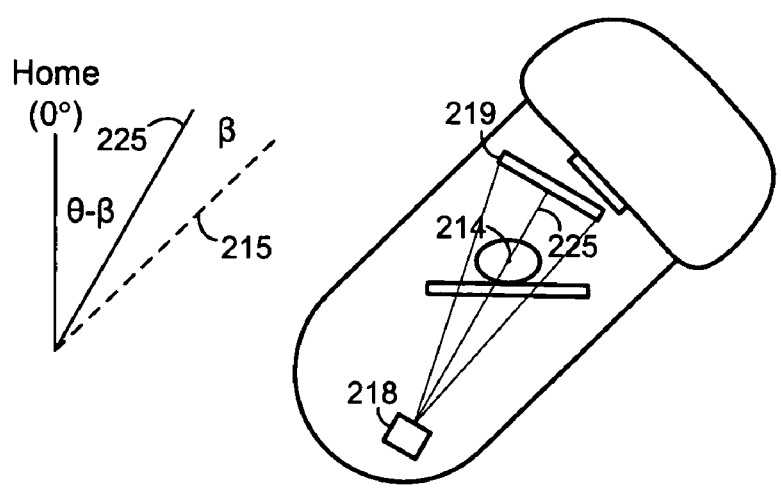
Figure 8C:
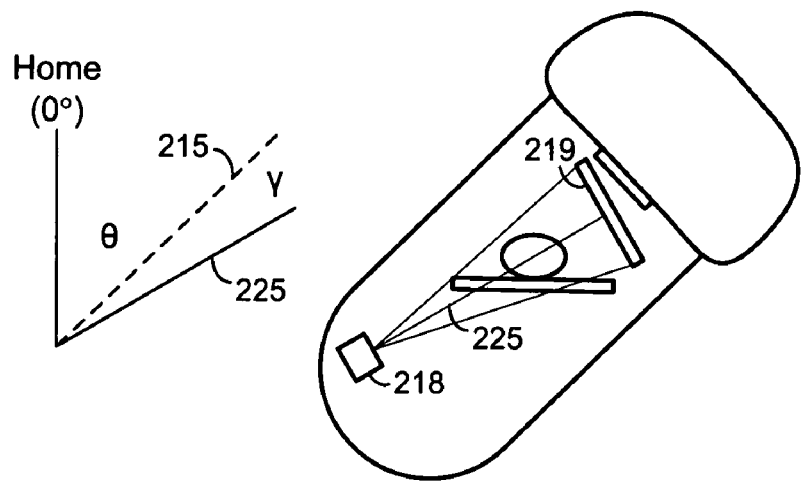

The apparatus of treatment room 200 may be used in some embodiments to implement process 300 and/or process 500 described above. In this regard, FIGS. 8A through 8C illustrate some embodiments of creating projection images of a target and performing digital tomosynthesis while a treatment delivering x-ray source is disposed at a treatment position. For clarity, support 222 is absent from FIGS. 8A through 8C.

FIG. 8A shows gantry 212 positioned such that beam axis 215 is disposed at angle θ with respect to the home position. X-ray detector 219 and kilovoltage x-ray source 218 are in line with beam axis 215. In FIG. 8B, x-ray detector 219 and kilovoltage x-ray source 218 have rotated about axis 214 by angle β. Kilovoltage x-ray beam axis 225 is therefore disposed at angle θ-β with respect to the home position.

FIG. 8C illustrates creation of a second projection image in which kilovoltage x-ray source 218 and detector 219 have rotated about axis 221 to the illustrated positions. Kilovoltage x-ray beam axis 225 defines an angle γ with beam axis 215. Kilovoltage x-ray beam axis 225 is therefore disposed at angle θ+γ with respect to the home position. As described above, some embodiments may include creation of a projection image at each of several angular intervals between the angles θ-β and θ+γ.

Figure 9A:
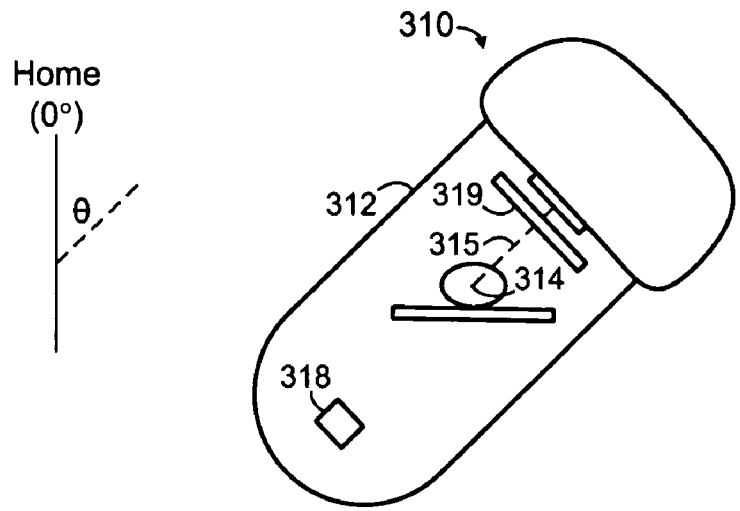
FIGS. 9A through 9C comprise front views of a treatment device to illustrate process steps according to some embodiments.
Figure 9B:
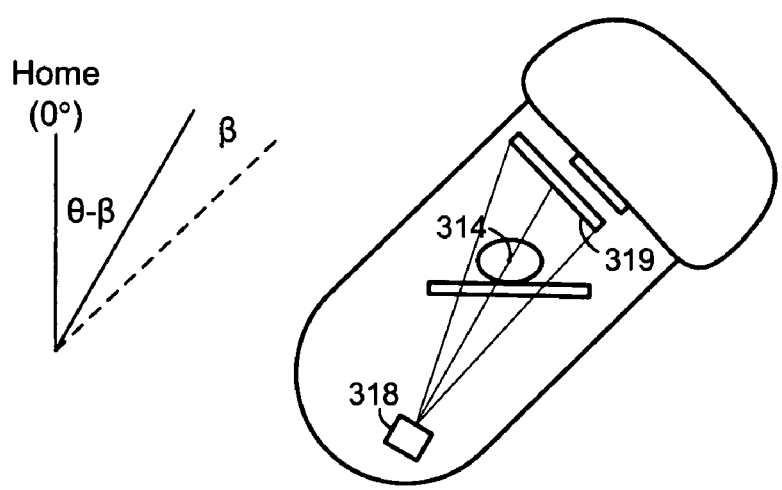
Figure 9C:
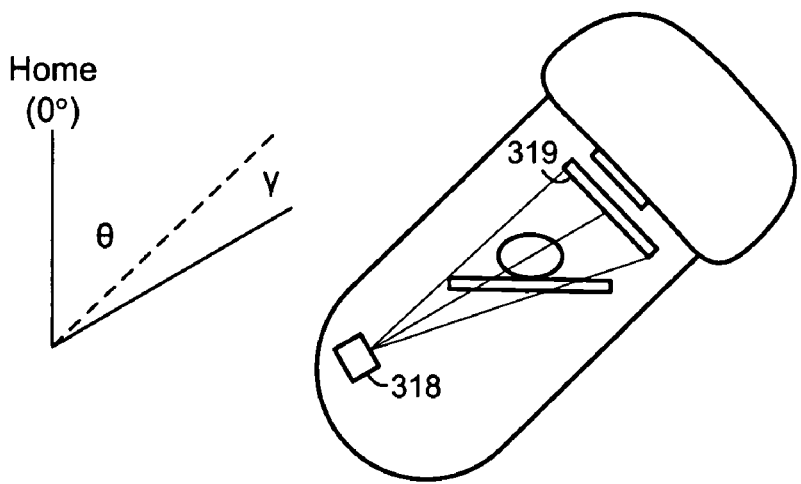

FIGS. 9A through 9C illustrate additional embodiments in which projection images of a target are created and digital tomosynthesis is performed while a treatment delivering x-ray source is disposed at a treatment position. Linac 310 includes kilovoltage x-ray source 318 which is rotatable about axis 314 as described with respect to source 218, and kilovoltage x-ray detector 319 which translates in a plane orthogonal to megavoltage x-ray beam axis 315 as described with respect to detector 119.

Gantry 312 is positioned at FIG. 9A such that beam axis 315 is disposed at angle θ with respect to the home position, and kilovoltage x-ray detector 319 and kilovoltage x-ray source 318 are in line with beam axis 315. In FIG. 9B, kilovoltage x-ray source 318 has rotated about axis 314 by angle β and detector 319 has translated such that a center of detector 319 intercepts kilovoltage beam axis 325. Kilovoltage x-ray beam axis 225 is disposed at angle θ-β with respect to the home position.

In FIG. 9C, kilovoltage x-ray source 318 has rotated about axis 314 by angle γ and detector 319 has translated such that a center of detector 319 again intercepts kilovoltage beam axis 325. Kilovoltage x-ray beam axis 325 is therefore disposed at angle θ-γ with respect to the home position. Projection images may be created using the systems of FIG. 9B and FIG. 9C. Subsequent correction of the projection images and/or digital tomosynthesis using the projection images may take into account the geometric relationships of source 318 and detector 319 during creation of the images using known mathematical techniques. The digital tomosynthesis algorithm used to generate the cross-sectional image accounts for these relationships in some embodiments.

Figure 10A:
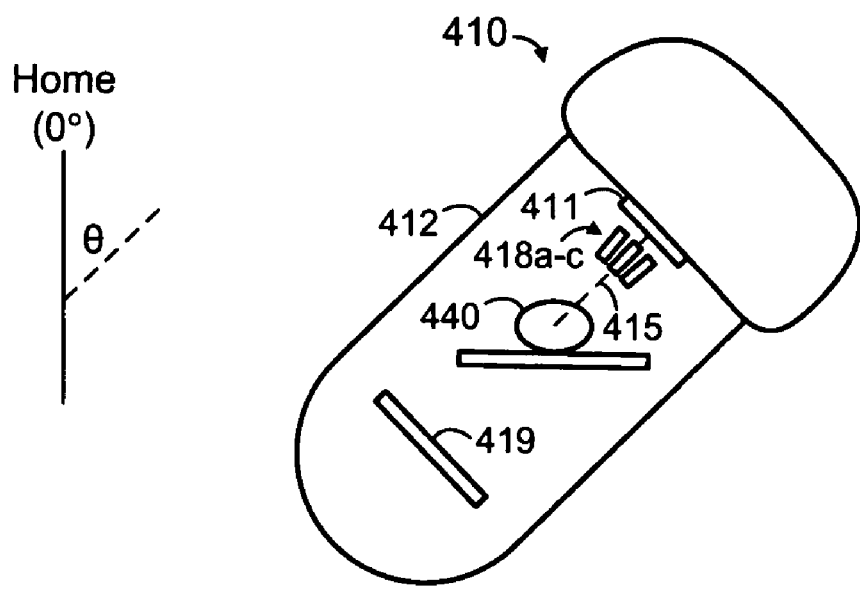
FIGS. 10A and 10B comprise front views of a treatment device to illustrate process steps according to some embodiments.
Figure 10B:
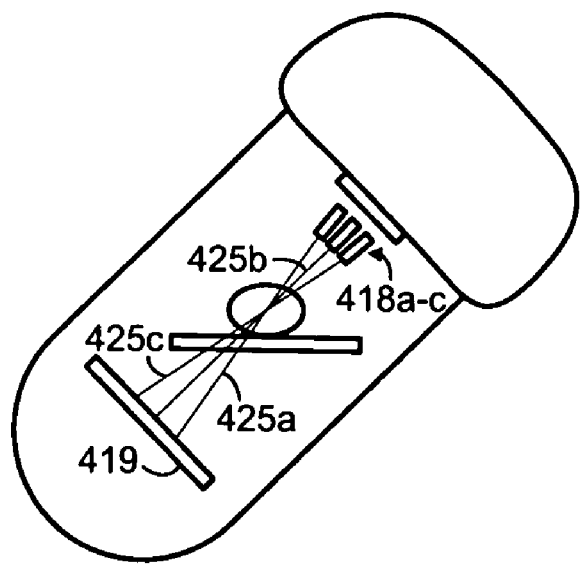

FIGS. 10A and 10B illustrate additional embodiments for creating projection images of a target and performing digital tomosynthesis while a treatment delivering x-ray source is disposed at a treatment position. Linac 410 includes imaging x-ray sources 418a-c disposed between treatment head 411 and object 440 and x-ray detector 419 which lies in a plane orthogonal to megavoltage x-ray beam axis 415 but located beyond object 440.

According to some embodiments, imaging x-ray sources 418a-c are fixed to treatment head 411. For example, sources 418a-c may be distributed along the circumference of treatment head 411. Sources 418a-c may be movable with respect to one another and/or treatment head 411 in some embodiments.

In FIG. 10A, beam axis 415 is disposed at angle θ with respect to the home position, and x-ray detector 419 is in line with beam axis 415. As shown in FIG. 10B, x-ray sources 418a-c may each emit an x-ray beam toward detector 419. The emitted beams exhibit one of beam axes 425a-c, each of which may pass through a patient isocenter. The beams may be emitted in succession while detector 419, sources 418a-c and treatment head 111 remain fixed, thereby creating a single projection image corresponding to each of sources 418a-c. If the angular spread of the beams is too large with respect to the size of detector 419, detector 419 may translate within its plane to receive successive x-ray beams from each of sources 418a-c.

The projection images may be corrected or otherwise modified prior to digital tomosynthesis to account for the geometric relationships between detectors 418a-c and detector 419 using known mathematical techniques. In some embodiments, the digital tomosynthesis algorithm used to generate the cross-sectional image accounts for these relationships.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    moving a treatment delivering x-ray source to a treatment position;
    creating projection images of a target using an imaging x-ray source while the treatment delivering x-ray source is disposed at the treatment position; and
    performing digital tomosynthesis on the projection images while the treatment delivering x-ray source is disposed at the treatment position to generate a cross-sectional image of the target.

2. A method according to claim 1, further comprising:
    determining whether to deliver an x-ray beam from the treatment delivering x-ray source according to a treatment plan based on the cross-sectional image.

3. A method according to claim 2, wherein determining whether to deliver the x-ray beam comprises:
    comparing the cross-sectional image with an expected image generated based on the treatment plan.

4. A method according to claim 2, further comprising:
automatically delivering the x-ray beam according to the treatment plan if it is determined to deliver the x-ray beam.

5. A method according to claim 1, further comprising:
automatically modifying a characteristic of an x-ray beam to be delivered by the treatment delivering x-ray source based on the cross-sectional image.

6. A method according to claim 1, wherein creating the projection images comprises:
moving the imaging x-ray source independently of the treatment delivering x-ray source.

7. A method according to claim 6, wherein moving the imaging x-ray source comprises:
translating the imaging x-ray source in a plane normal to a beam axis of the treatment delivering x-ray source at the treatment position; and
pivoting the imaging x-ray source about an axis passing through the imaging x-ray source.

8. A method according to claim 7, wherein creating the projection images further comprises:
moving an x-ray detector in a plane normal to the beam axis of the treatment delivering x-ray source.

9. A method according to claim 6, wherein moving the imaging x-ray source comprises:
moving the imaging x-ray source about an axis intersecting the target.

10. A method according to claim 9, wherein moving the imaging x-ray source to create the projection images further comprises:
moving an x-ray detector in a plane normal to a beam axis of the treatment delivering radiation source.

11. A method according to claim 9, wherein moving the imaging x-ray source to create the projection images further comprises:
moving an x-ray detector about the axis intersecting the target.

12. A method according to claim 1, wherein creating the projection images comprises:
emitting a respective x-ray beam from each of a plurality of sources of the imaging x-ray source,
wherein the imaging x-ray source is stationary with respect to the treatment delivering x-ray source during creation of the projection images.

13. A method according to claim 1, further comprising:
moving the treatment delivering x-ray source to a second treatment position;
creating second projection images using the imaging x-ray source while the treatment delivering x-ray source is disposed at the second treatment position; and
performing digital tomosynthesis on the second projection images while the treatment delivering x-ray source is disposed at the second treatment position to generate a second cross-sectional image of the target.

14. An apparatus comprising:
a treatment delivering x-ray source to deliver a treatment x-ray beam from a treatment position;
an imaging x-ray source to deliver an imaging x-ray beam;
an x-ray detector to acquire projection images of a target based on the imaging x-ray beam while the treatment delivering x-ray source is disposed at the treatment position; and
a processor to perform digital tomosynthesis on the projection images while the treatment delivering x-ray source is disposed at the treatment position to generate a cross-sectional image of the target.

15. An apparatus according to claim 14, the processor further to:
determine whether to deliver the treatment x-ray beam from the treatment delivering x-ray source based on the cross-sectional image and an expected image generated based on the treatment plan.

16. An apparatus according to claim 15, the processor further to:
instruct the treatment delivering x-ray source to automatically deliver the treatment x-ray beam according to the treatment plan if it is determined to deliver the x-ray beam.

17. An apparatus according to claim 14, the processor further to:
automatically modify a characteristic of the treatment x-ray beam to be delivered by the treatment delivering x-ray source based on the cross-sectional image.

18. An apparatus according to claim 14, wherein the imaging x-ray source is to move independently of the treatment delivering x-ray source during acquisition of the projection images.

19. An apparatus according to claim 18, wherein the imaging x-ray source is to translate in a plane normal to a beam axis of the treatment delivering x-ray source at the treatment position during acquisition of the projection images, and
wherein the imaging x-ray source is to pivot about an axis passing through the imaging x-ray source during acquisition of the projection images.

20. An apparatus according to claim 19, wherein the x-ray detector is to move in a plane normal to the beam axis of the treatment delivering x-ray source during acquisition of the projection images.

21. An apparatus according to claim 18, wherein the imaging x-ray source is to rotate about an axis intersecting the target during acquisition of the projection images.

22. An apparatus according to claim 21, wherein the x-ray detector is to move in a plane normal to the beam axis of the treatment delivering x-ray source during acquisition of the projection images.

23. An apparatus according to claim 21, wherein the x-ray detector is to move about the axis intersecting the target during acquisition of the projection images.

24. An apparatus according to claim 14, wherein the imaging x-ray source comprises a plurality of sources to deliver respective ones of a plurality of x-ray beams, and
wherein the imaging x-ray source is stationary with respect to the treatment delivering x-ray source during acquisition of the projection images.

25. An apparatus according to claim 14, wherein the treatment delivering x-ray source is to deliver a treatment x-ray beam from a second treatment position,
wherein the x-ray detector is to acquire second projection images of the target based on a second imaging x-ray beam while the treatment delivering x-ray source is disposed at the second treatment position, and
wherein the processor is to perform digital tomosynthesis on the second projection images while the treatment delivering x-ray source is disposed at the second treatment position to generate a second cross-sectional image of the target.

* * * * *